US 8,486,071 B2

(12) United States Patent
Jensen et al.

(10) Patent No.: US 8,486,071 B2
(45) Date of Patent: Jul. 16, 2013

(54) SHORT PIN FOR TAKING CARE OF EPIPHYSIS FRACTURES

(75) Inventors: Harm-Iven Jensen, Noer (DE); Ole Lueckert, Kiel (DE)

(73) Assignee: Tantum AG, Neumuenster (DE)

( * ) Notice: Subject to any disclaimer, the term of this patent is extended or adjusted under 35 U.S.C. 154(b) by 77 days.

(21) Appl. No.: 13/058,710

(22) PCT Filed: Aug. 7, 2009

(86) PCT No.: PCT/EP2009/005895
§ 371 (c)(1),
(2), (4) Date: Feb. 11, 2011

(87) PCT Pub. No.: WO2010/017990
PCT Pub. Date: Feb. 18, 2010

(65) Prior Publication Data
US 2011/0137313 A1  Jun. 9, 2011

(30) Foreign Application Priority Data
Aug. 12, 2008  (DE) ...................... 20 2008 010 922 U

(51) Int. Cl.
*A61B 17/58* (2006.01)
(52) U.S. Cl.
USPC .......................................................... 606/64
(58) Field of Classification Search
USPC ................... 606/62–68, 70, 71, 96, 280, 281, 606/286, 295, 301
See application file for complete search history.

(56) References Cited

U.S. PATENT DOCUMENTS

| 5,041,114 | A | * | 8/1991 | Chapman et al. | 606/62 |
| 5,041,116 | A | * | 8/1991 | Wilson | 606/65 |
| 5,472,444 | A | * | 12/1995 | Huebner et al. | 606/64 |
| 5,693,055 | A | | 12/1997 | Zahiri et al. | |
| 7,118,572 | B2 | * | 10/2006 | Bramlet et al. | 606/66 |

(Continued)

FOREIGN PATENT DOCUMENTS

| DE | 9106152 U1 | 10/1991 | |
| EP | 1486175 | * 5/2004 | 606/62 |

(Continued)

OTHER PUBLICATIONS

International Search Report of PCT/EP2009/005895 Dated Nov. 25, 2009 With an English Translation.

*Primary Examiner* — Pedro Philogene
(74) *Attorney, Agent, or Firm* — Venable LLP; Robert Kinberg; Tamatane J. Aga

(57) ABSTRACT

A short nail for treatment of an epiphyseal fracture close to a joint in a long bone includes a two part nail supporting body comprising a main body having a transverse through-bore and releasably attached to a stub body. The stub body has an end that has a diaphyseal slant. The stub body and the lateral slant form part of a diaphyseal anchor which is attachable to the main body via the stub body and which has a flat connecting web that has an oblique orientation and ending laterally in a plane with the diaphyseal slant. A connecting device rigidly and releasably connects the main body and the stub body together. An anchoring device fixes the flat web in flat abutment against the diaphysis. A fixation pin is insertable into the transverse through-bore in a crossed arrangement with, and at a fixed angle to, the supporting body in the state of treatment of the fracture. The fixation pin includes a mechanism to protect against axial movement of the pin.

11 Claims, 3 Drawing Sheets

U.S. PATENT DOCUMENTS

| | | | |
|---|---|---|---|
| 8,137,350 B2 * | 3/2012 | Nakamura | 606/65 |
| 8,182,484 B2 * | 5/2012 | Grant et al. | 606/66 |
| 2002/0049445 A1 | 4/2002 | Hall, IV et al. | |

FOREIGN PATENT DOCUMENTS

| | | | | |
|---|---|---|---|---|
| EP | 1486175 A | 12/2004 | | |
| WO | WO-2004/039271 | | 5/2004 | |
| WO | WO2004/039271 | * | 5/2004 | 606/64 |
| WO | WO-2007/035440 | | 3/2007 | |
| WO | WO2007/035440 | * | 3/2007 | 606/64 |

* cited by examiner

SHORT PIN FOR TAKING CARE OF EPIPHYSIS FRACTURES

CROSS-REFERENCE TO RELATED APPLICATION

The present application is a U.S. National Stage of International Application No. PCT/EP2009/005895, filed on Aug. 7, 2009, designating the United States, and claiming to German Patent Application No. 20 2008 010 922.1, filed Aug. 12, 2008.

BACKGROUND OF THE INVENTION

The invention concerns a short nail for the treatment of epiphyseal fractures close to the joint in a long bone having epiphysis and diaphysis, comprising a nail supporting body adapted to the dimensions of the fractured epiphysis and designed to be introduced with a lateral access path remote from the joint, and, in the state of treatment of the fracture, at least one fixation pin which passes through the nail supporting body in a crossed arrangement through a transverse through-bore and which is provided with mounting at a fixed angle on the supporting body and with protection against movement along the axis of the pin, wherein the supporting body is dimensioned and designed in such a way that it comes to lie in an oblique position in the fractured epiphysis and its end which comes to lie on the lateral side of introduction has a diaphyseal slant which ends at least almost flush at the outer circumference of the diaphysis in a region of the diaphysis which adjoins the metaphysis extending between the fractured epiphysis and the diaphysis.

With the short nail there is provided an intramedullary implant which supports and sustains the existing bone structure. In essential contrast to longitudinally extending bone nails, for example for treating fractures of the upper arm, which are introduced in antegrade fashion close to the joint and anchored in the marrow cavity of the diaphysis (cf. for example U.S. Pat. No. 5,472,444), the short nail allows a surgical technique which is minimally invasive and which supports and sustains the existing bone structure of the epiphysis even in the case of problematic fractures. The joint is not opened. The access path percutaneously from the side reduces the tissue trauma. The stabilisation of epiphyseal fragments is effected by the crossed fixation pins. Such a system is especially suitable for subcapital and pertubercular fractures of the humerus.

The surgical technique with a short nail is also to be distinguished from surgical techniques with plate systems. For example, a plate assembly with a bone screw subjected to compression is known from U.S. Pat. No. 5,693,055. The bone screw is introduced in an oblique arrangement laterally through the diaphysis. However, the screw is a clamping screw which as such does not form a supporting body for locking/fixation pins, in that it has to be clamped against a plate to be mounted in the region of diaphysis and metaphysis in order to pull bone fragments together. A part of the plate is to be introduced into a special counterbore of the diaphysis. The screw which is under compression cannot cover and stabilise multiple-fragment fractures. Other known systems with plates which are attached to the bone in the region close to the joint and which serve as load-bearing members for locking screws (e.g. DE-T2-602 20 175) can be used for treatment only under certain conditions and with restrictions. In particular, there is the requirement of surgery close to the joint. The surgical technique is particularly invasive and leads to traumatisation. With the plate systems, short fracture segments cannot be encompassed.

A generic short nail for treating head fractures of a bone is disclosed in WO-A2-2004039271. Even though the short nail described there substantially improves the surgical technique and the treatment of particularly problematic multiple-fragment fractures, it has been revealed that fixation elements in the region of the surgical neck in some applications are not sufficient for satisfactory stabilisation of the short nail. The invention is intended to provide a remedy for this.

SUMMARY OF THE INVENTION

Accordingly, it is the aim of the invention to improve stabilisation of the short nail and extend surgical indications.

The aim is achieved in connection with the features of the short bone nail of the kind mentioned hereinbefore, by the fact that the supporting body is constructed in two parts with a main body having the at least one transverse through-bore for the fixation pin and a stub body which has the diaphyseal slant and which is provided with a supporting cross-section corresponding to the main body and forms a fixed part of a diaphyseal anchor which can be releasably attached to the main body by means of the stub body and a connecting means rigidly connecting the main body and the stub body and which is designed with a flat connecting web which in oblique orientation with the diaphyseal slant ends laterally in a plane with the latter, comes to abut flat against the diaphysis, pointing away from the fractured epiphysis, and is provided with an anchoring means by which the flat web can be fixed in flat abutment against the diaphysis.

According to the invention, the result is that the implanted short nail is particularly effectively and reliably stabilised. The supporting body of the short nail is constructed and designed with the diaphyseal anchor in such a way that, without effect on the nail length and hence without impairing the oblique position in the fractured epiphysis, the stable supporting function is guaranteed, and breaking off towards the bone shaft is reliably avoided. It is essential that the stub or extension body of the supporting body with the diaphyseal slant forms part of the diaphyseal anchor, so that the supporting body ends flush with the diaphyseal slant at the diaphyseal anchor or at its flat connecting web. The result of the flat connecting web is that the diaphyseal slant ends at least almost flush at the outer circumference of the diaphysis.

A fixing part of the flat connecting web is determined by a flat-shaped extension piece after the fashion of a flat lug or tongue. Thus the flat connecting web is not bulky at the circumference of the diaphysis. Although the stable oblique position of the short nail in the fractured epiphysis, extending into the region of the metaphysis or the surgical neck, is achieved, it is possible to achieve anchoring in the region of the diaphysis remote from the joint, and there with an anchoring means which is easy to attach and reduces traumatisation, appropriately with a connecting screw screwed into the diaphysis. Force conditions for fixing the supporting body with support and stability are particularly favourable, as the flat connecting web of the diaphyseal anchor merges with the stub body of the supporting body laterally on the outside at a shallow obtuse angle. The flat connecting web remains particularly flat with a relatively small surface area while guaranteeing supporting and fixing functions with the anchorage laid in the diaphysis under the sloping end of the supporting body. Preferably the flat connecting web is kept so short that the anchorage comes to lie in the vicinity of the sloping end of the supporting body, under the latter. On account of the design according to the invention, particular engagement of the diaphyseal anchor in the diaphysis is avoided.

Overall, a short nail implant is obtained whose supporting body, which serves as the intra-medullary load-bearing member, is stabilised to a particular extent is obtained. The result is optimum stabilisation of the head fragments by means of the fixation pins. Stable treatment of the fracture, particularly even with multiple-fragment fractures, is achieved for both vital and porotic bone structures. Advantages of minimally invasive surgical techniques, hence in particular preservation of the bonehead, gentle treatment of ligaments and tendons as a prerequisite for good reduction results as well as avoidance of traumatisation during treatment come into their own.

The anchorage according to the invention is particularly advantageously provided in combination with an external thread formed at the bone-engaging end of the supporting body. The result is that the supporting body is fixed at both outer ends.

Appropriately, the connecting means which connects the main body and the stub body of the supporting body consists of a screw connection. The connection is rigid in the sense that the main body and the stub body are pulled towards each other end to end so as to be protected against displacement and rotation relative to each other.

The connecting means which connects the main body and the stub body of the supporting body can be designed with means for protection against rotation, which blocks relative axial rotation between the two bodies in an adjustable rotational position in a positive and/or non-positive locking relationship.

An advantageous embodiment also consists in that the anchoring means of the diaphyseal anchor is designed with a catch means which forms at least two catch positions which in each case determine a height of the diaphyseal anchor on the diaphysis and which can be selected and protect the diaphyseal anchor in the fixed state against movement directed away from the epiphysis along the diaphysis.

In an advantageous design, the stub body is constructed with a cavity open at the diaphyseal slant and forming a passage, and the screw connection which connects the diaphyseal anchor rigidly to the main body of the supporting body comprises a connecting screw which can be inserted laterally and which has a head region which becomes at least substantially countersunk in the cavity. Particularly simple anchoring of the diaphyseal anchor is obtained by the fact that the anchoring means comprises an elongated hole extending according to the diaphysis and formed at its flat connecting web, and an anchoring screw which can be passed through the elongated hole. Appropriately, a design of the aforementioned catch means consists in that the elongated hole is constructed as a catch positioning pattern device for holding the head of the anchoring screw with variable height in catched relationship.

Appropriately, the stub body of the supporting body and the flat connecting web have such small dimensions and design that the flat connecting web ends flush at the stub body, ending at least almost rimlessly with the stub body on the side of the metaphysis.

A peculiarity of the supporting body according to the invention lies in that the lateral end of the supporting body in the form of the stub body is constructed as the base or foot of the diaphyseal anchor. Appropriately, the stub body forms an integral part of the diaphyseal anchor and is formed together with the latter. The supporting body which is in two parts and comprises the diaphyseal anchor can be manufactured and provided as a unit for the implant.

The short nail according to the invention is appropriately provided in the form of an entity of items which forms a sales unit. The entity of items for producing a short nail implant, in particular for proximal fractures of the humerus, comprises the parts of the short nail or supporting body according to the invention, namely at least in the singular in each case the main body, the diaphyseal anchor with stub body, the connecting means and the anchoring means therefor, and also at least one set of fixation pins.

Dependent claims are directed at the aforementioned and other appropriate and advantageous embodiments. Particularly appropriate and advantageous embodiments or possible designs of the invention are described in more detail with the aid of the following description of the practical examples shown in the schematic drawings. These show:

DETAILED DESCRIPTION

The short nail 1 shown in the practical example is designed as an implant for subcapital and pertubercular fractures of the humerus 7. The short nail 1 is particularly suitable for the above-mentioned fractures of the humerus. Generally, the short nail according to the invention with adapted dimensions and design is particularly suitable for treating multiple-fragment fractures of the epiphyses of long bones, such as for example femur, tibia, fibula, radius and ulna. But the short nail designed according to the invention can also be used for other bones with fractures close to the joint, for example for fractures of the calcaneus.

Figure 1:
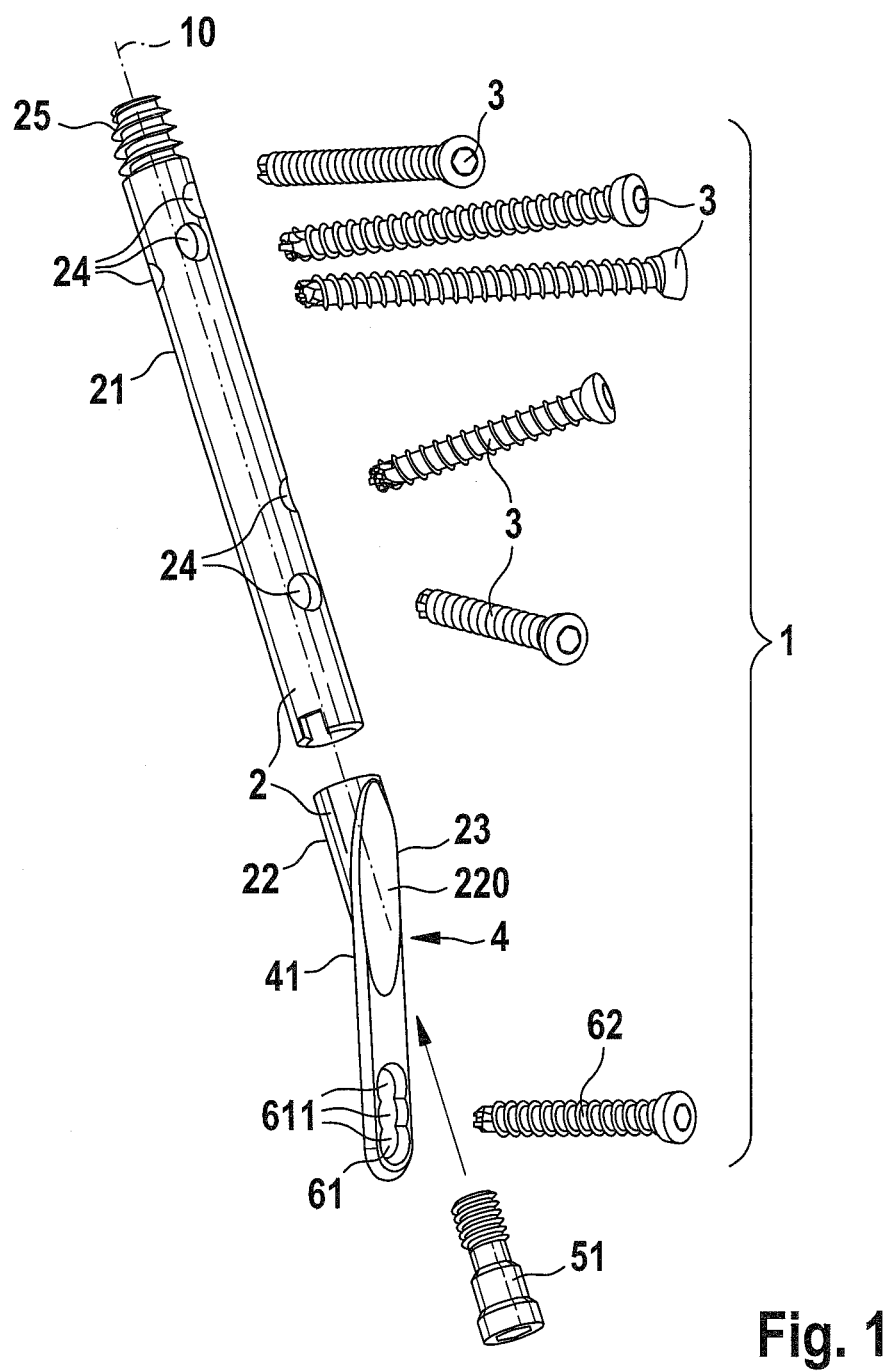
FIG. 1 in an exploded view and front side view, a short nail according to the invention for treating a multiple-fragment fracture of the humerus, FIG. 2 in a view from the rear, the short nail according to the invention assembled from the parts of FIG. 1 as an implant in the humerus and FIGS. 3 and 4 the bone nail according to FIGS. 1 and 2 in a view from the rear and the side, respectively.
Figure 2:
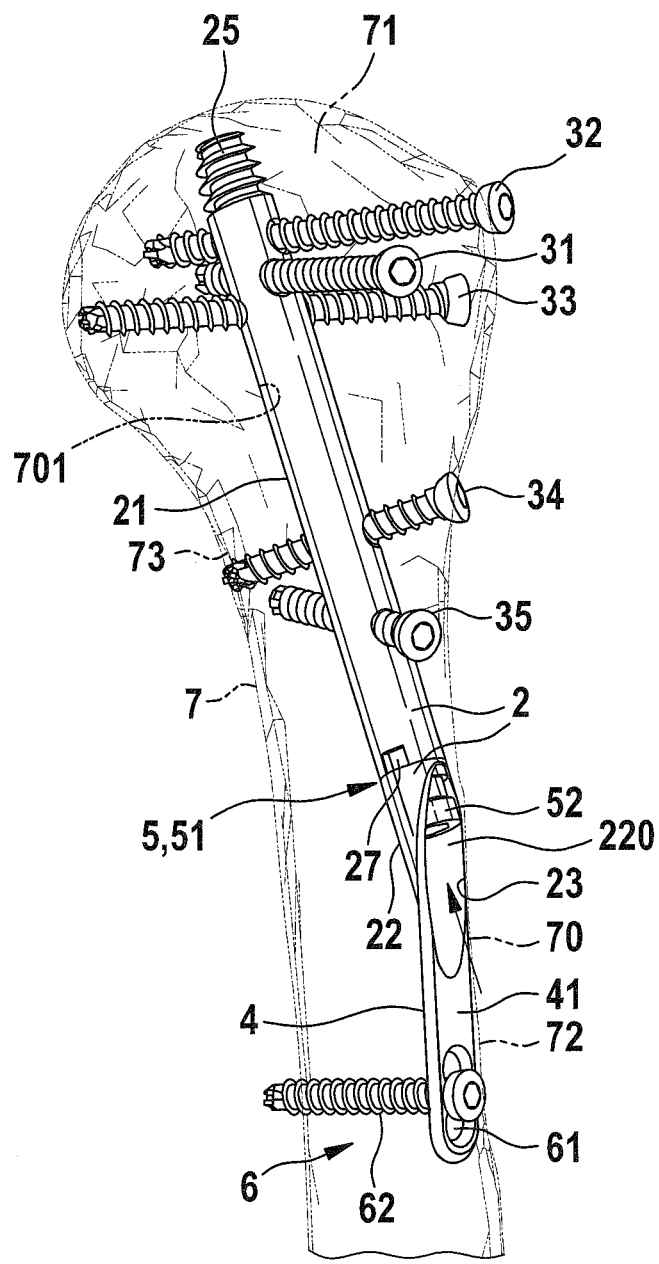

FIG. 2 shows the position, structure and assembly of the short nail 1 implanted in the humerus 7. Fracture lines are not shown in more detail in the head 71 of the humerus (epiphysis of the humerus). Individual components of the short nail 1 can be seen from FIG. 1. The short nail 1 has a supporting body 2, fixation pins 3, a diaphyseal anchor 4 and also a connecting means 5 and an anchoring means 6.

The supporting body 2 is constructed in two parts. In the form of a rod or nail with a smooth shaft, it has the function of a load-bearing member in connection with the fixation pins 3 which pass through it. It is composed of an elongate straight main body 21 and a comparatively short stub or base body 22. In the embodiment the two bodies 21, 22 have a corresponding and constant circular cross-section, and they are designed as hollow cylinders. By means of the connecting means 5 the two bodies 21, 22 are rigidly and permanently assembled together in straight alignment, butted together at facing ends with abutting surfaces perpendicular to the straight nail axis 10. The connection is such that the two bodies 21, 22 fit together so as to be non-rotatable and axially non-displaceable relative to each other.

Viewed in more detail, the stub body 22 has the form of an obliquely cut-off piece of a hollow circular cylinder. The oblique cut and the oblique surface are at an obtuse wide angle 26 to the longitudinal axis 10 of the short nail 1. The oblique surface forms a diaphyseal slant 23 ending flush with the diaphyseal surface, at the end of the supporting body which comes to lie at the lateral side of introduction of the short nail 1.

The diaphyseal anchor 4 is designed or formed as a single-piece or single-part component which in any case forms a fixed body unit. Constituents are a flat connecting web 41 and the stub body 22. The flat web 41 comprises a flat elongate piece after the fashion of a fixing lug or tongue which projects exclusively distally at the stub body 22, that is, directed away from the head 71 (fractured epiphysis) of the humerus. The diaphyseal anchor 4 is designed in such a way that the diaphyseal slant 23 merges with the lateral flat surface of the flat web 41 or coincides with it. The diaphyseal slant 23 is open at the flat surface of the diaphyseal anchor 4 which extends in elongate fashion at the circumference of the diaphysis 72. The stub body 23 merges rimlessly flush with the flat surface and hence with the flat web 41. This junction is proximally flush and rimless, so that it is only distally that the diaphyseal anchor 4 with the flat web 41 comes into positive locking flat abutment with the substantially straight wall of the diaphysis 72. Also, the stub body 22 is such a short piece that the flat web 41 or the oblique opening corresponding to the diaphyseal slant 23 ends without overhang with the stub body 22 proximally, that is, on the side of the fractured metaphysis 73. In other words, the connecting surface of the stub body 22 which forms the butt fit ends proximally with the flat surface of the diaphyseal anchor 4 and does not protrude beyond it proximally.

With the short stub body 22 of the diaphyseal anchor 4 described, the result achieved to a particular extent is that the connection of the diaphyseal anchor 4 to the main body 21 of the supporting body 2 is made laterally as far as possible, but countersunk in the diaphysis 72.

The connecting means 5 is designed as a screw connection 51 with a connecting screw 52. The latter engages in an internal thread on the inside at the distal end of the main body 21 and with its head comes to lie in the passage or cavity 220 of the stub body 22 in a countersunk arrangement. The connecting ends of the two bodies 21, 22, which are butted together by means of the screw connection 51, form in non-positive locking relationship a means for preventing rotation, which blocks relative axial rotation between the two bodies 21, 22 in an adjustable position. Fine adjustment of the rotational position of the bodies 21, 22 relative to each other is important to produce flat abutment of the flat web 41 against the diaphysis 42 over a large surface area. The adjustable rotational position can for example also be set up by a finely adjusting catch connection with detent disks or the like.

The main body 21 of the supporting body 2 has in its lateral end face a groove 27 for the connection of a conventional adapter for sighting mechanism and turning tool for alignment and introduction of the main body 21 of the nail.

The diaphyseal anchor 4 is fixed to the diaphysis 72 by means of the flat connecting web 41 distally beneath the sloping end surface 23 of the short nail 2 in the vicinity of the nail end. This anchoring connection comprises as the anchoring means 6 an anchoring screw 62 with full thread as well as an elongated hole 61 in the flat web 41 extending lengthways with the diaphysis 72. The anchoring means comes to lie at the diaphysis 72 in a relatively fixed region of the humerus 1, and it is not particularly bulky at the circumference of the diaphysis 72 with the flat web 41 of the diaphyseal anchor 4 which is particularly flat and has a small surface area. Advantageously, the fixing part of the flat web 41 can be made so elastic and hence so thin that, after attachment of the connecting means 5 and anchoring means 6, it fits snugly against the diaphysis wall. The connection of the distal end of the supporting body with the anchoring screw 62 or some other suitable connecting means, even via the web 41 which is elastic for close elastic fitting, proves to be sufficiently effective for stabilisation according to the invention.

As can be seen in particular from FIG. 1, the elongated hole 61 at the inner edge is formed with three catch holes 611 which, when the screw connection is tightened, in each case receive the head of the anchoring screw 62 in a fixed latch fit, whereas when the screw connection is not tightened, a passage is formed for the shaft of the anchoring screw 62 over the length of the elongated hole 61. With this arrangement the diaphyseal anchor 4 can optionally be fixed in three catch positions that determine its height at the diaphysis 72.

Figure 4:
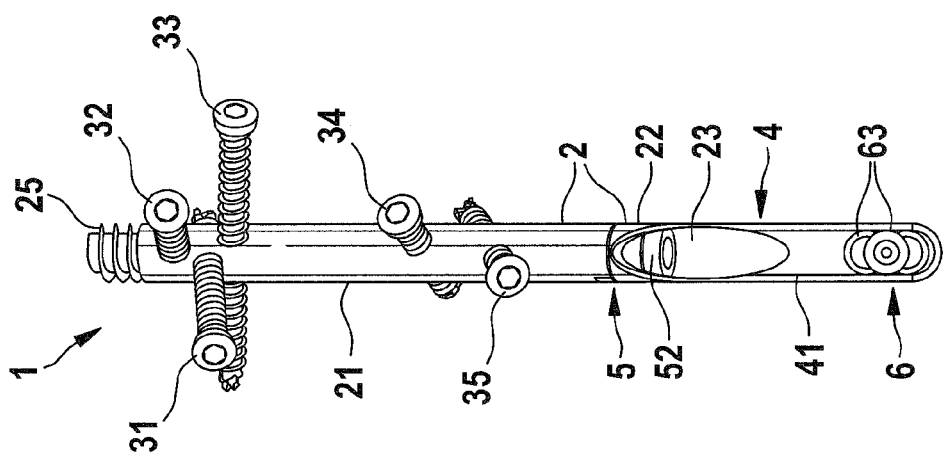
Figure 3:
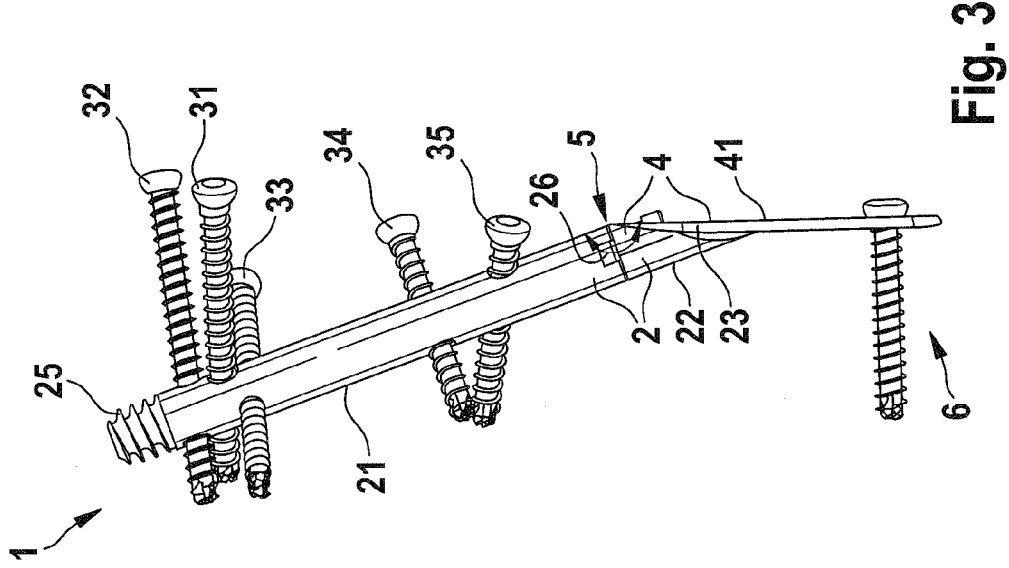

In the embodiment of FIGS. 2 to 4, the screw head is seated in the central catch seat. Each catch seat protects the fixed diaphyseal anchor 4 in a simple manner against movement directed away from the epiphysis 71 along the diaphysis 72. At the desired height, particularly effective support in a direction transversely to the shaft of the anchoring screw 62 is obtained. Other suitable catch connections or similar locking connections which adjust the height of support can be set up. In this case the connecting/anchoring elements are designed and dimensioned in such a way that the arrangement at the diaphysis 72 corresponding to the flat dimension of the flat web 41 remains particularly flat.

The fixation pins 3, as can be seen from FIGS. 1 to 4, are designed as screws with a thread extending over its length (full thread), appropriately as cannulated banjo screws. These are in each case passed through internally threaded transverse through-bores 24 which are provided exclusively in the main body 21 of the supporting body 2, this being in such a way that the screws 3 come to lie in a crossing arrangement. Each screw (each fixation pin) 3 is attached by means of the screw connection at a fixed angle to the supporting body 2 and with protection against movement along the screw axis.

As can be seen from FIG. 2, the short nail 1 or the supporting body 2 comes to lie in a special oblique arrangement substantially in the head 71 (fractured epiphysis) of the humerus. The supporting body 2 is dimensioned and arranged in such a way that, starting from its distal end in the region of the surgical neck of the bone, it extends into the medial region of the head 71 of the humerus. The proximal end of the supporting body 2 is provided with an external thread 25. This thread 25 is self-tapping and anchors the supporting body 2 at its bone-engaging end. This anchorage cooperates particularly well with the distal lateral anchorage by means of the diaphyseal anchor 4 according to the invention.

The implant is made by implanting the short nail 1, using ordinary instruments and tools such as in particular sighting mechanism, drilling tools, guide rods and sleeves. First the main body 21 is introduced, on a lateral access path 70 remote from the joint, with a solid fit into a previously formed drill hole 701 which serves to receive the supporting body 2 and is uniform over its whole length with the same cross-section. Then for example the screw 31 can be introduced for fixing the Tuberculum minus. Then the screws 32 and 33 are introduced for fixing the Tuberculum majus. These screws, which are carried by the supporting body 2, in each case connect fragments after reduction. They each pass through a terminal fracture surface (not shown) and hold the fragments together by screw connection. Finally the diaphyseal anchor 4 is joined to the base 22 of the supporting body by the connecting means 5. Anchorage with the means 6 is effected distally, remote from the fracture spur which is deepest at the epiphysis 71.

In the embodiment the short nail 1 also has fixation screws (fixation pins) 34, which are screwed in the region of the surgical neck or in the region of the metaphysis and serve to stabilise the short nail 2 instead of anchoring with a proximal thread 25 or additionally in its longitudinal region in a firmer region of the bone. Also essentially important in this respect is countersunk attachment of the diaphyseal anchor 4 according to the invention to the outermost distal end of the supporting nail 2 with anchorage remote from the fracture region in solid bone material of the straight diaphysis 72.

The invention claimed is:

1. A short nail for treatment of an epiphyseal fracture close to a joint in a long bone having an epiphysis and a diaphysis, comprising:
   a two part nail supporting body adapted to dimensions of the fractured epiphysis and constructed to be introduced into the bone with a lateral access path remote from the joint, the two part nail supporting body comprising a main body having at least one transverse through-bore and a stub body releasably attachable to the main body and having a supporting cross-section corresponding to the main body, wherein the two part supporting body is dimensioned and constructed to come to lie in an oblique position in the fractured epiphysis, wherein the stub body has an end which comes to lie on a lateral side of introduction and which has a diaphyseal slant ending at least almost flush at the outer circumference of the diaphysis in a region of the diaphysis which adjoins a metaphysis extending between the fractured epiphysis and the diaphysis, wherein the stub body and the lateral slant form part of a diaphyseal anchor which is attachable to the main body via the stub body and which has a flat connecting web that has an oblique orientation and which ends laterally in a plane with the diaphyseal slant and comes to abut flat against the diaphysis, pointing away from the fractured epiphysis;
   a connecting device to rigidly and releasably connect the main body and the stub body together at abutting ends of the main body and stub body, respectively;
   an anchoring device to fix the flat web in flat abutment against the diaphysis; and
   at least one fixation pin having a longitudinal axis adapted to be inserted into the at least one transverse through-bore in a crossed arrangement with, and at a fixed angle to, the supporting body in the state of treatment of the fracture, wherein the fixation pin includes a mechanism to protect against movement along said longitudinal axis.

2. The short nail according to claim 1, wherein the supporting body has an end facing away from the stub body that includes an external thread.

3. The short nail according to claim 1, wherein the connecting device comprises a screw connection.

4. The short nail according to claim 3, wherein the stub body includes a cavity and the screw connection comprises a laterally insertable connecting screw with a head region which comes to lie at least substantially countersunk in the stub body cavity.

5. The short nail according to claim 1, wherein the connecting device includes a mechanism to protect against rotation of the main body and stub body relative to each other.

6. The short nail according to claim 1, wherein the anchoring device comprises an elongated hole formed in the flat connecting web and extending according to the diaphysis and an anchoring screw adapted to be passed through the elongated hole.

7. The short nail according to claim 1, wherein the anchoring device includes a catch that defines at least two selectable catch positions which, in each case, determine a height of the diaphyseal anchor on the diaphysis and which in a selected catch position protects the diaphyseal anchor in a fixed state against movement directed away from the epiphysis along the diaphysis.

8. The short nail according to claim 1, wherein the stub body and the flat connecting web are dimensioned and shaped so that the flat connecting web ends at least substantially without overhang with the stub body on the side of the metaphysis.

9. The short nail according to claim 6, wherein the elongated hole comprises the sole opening in the flat connecting web to receive an anchoring device to fix the flat web in flat abutment against the diaphysis.

10. A supporting body of a short nail for treatment of an epiphyseal fracture close to a joint in a long bone having an epiphysis and a diaphysis, the supporting body comprising a main body, a stub body, and a connecting device for rigidly and releasably connecting the main body and the stub body together at abutting ends of the main body and stub body, respectively, wherein the stub body is part of a diaphyseal anchor that is fixable in abutment to the diaphysis.

11. A kit to produce a short nail implant for a proximal fracture of a humerus, comprising:
   a two part supporting body including a main body having at least one transverse through-bore and a diaphyseal anchor having a stub body, a connecting device to releasably and rigidly connect the stub body and main body together, an anchoring device to fix the diaphyseal anchor to the humerus, and at least one fixation pin to insert into the through-bore of the main body in a state of treatment of the fracture.

* * * * *